United States Patent [19]

Mathew

[11] Patent Number: 5,089,611

[45] Date of Patent: Feb. 18, 1992

[54] ALKYL-2-THIOSUBSTITUTED-3-SUBSTITUTED-2-BUTENOATES AND THEIR SYNTHESIS

[75] Inventor: Jacob Mathew, Fenton, Mo.

[73] Assignee: Petrolite Corporation, St. Louis, Mo.

[21] Appl. No.: 492,511

[22] Filed: Mar. 12, 1990

[51] Int. Cl.$^5$ .................. C07D 279/02; C07C 67/30; C07C 323/14; C07C 323/19
[52] U.S. Cl. .......................... 544/3; 560/17; 560/152; 562/431; 562/598
[58] Field of Search ............... 560/17, 152; 562/431, 562/598; 544/3

[56] References Cited

PUBLICATIONS

Durman et al., Tetrahedron Letters, vol. 24, No. 20, pp. 2113–2116, (1983).

Takaki et al., J. Org. Chem., vol. 43, No. 3, pp. 402–405, (1978).

Rosnati et al., Gazzetta Chemica Italiana, vol. 111, pp. 249–256, (1981).

Primary Examiner—Jose G. Dees
Assistant Examiner—Vera C. Clarke
Attorney, Agent, or Firm—Jeffrey S. Boone; Kenneth Solomon

[57] ABSTRACT

An alkyl 2-thiosubstituted-3-substituted-2-butenoate

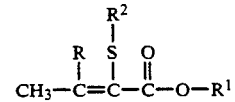

is prepared by reacting an alkyl 2-chloro-3-substituted-3-butenoate with a thio compound under phase transfer conditions.

9 Claims, No Drawings

ALKYL-2-THIOSUBSTITUTED-3-SUBSTITUTED-2-BUTENOATES AND THEIR SYNTHESIS

BACKGROUND OF THE INVENTION

This invention relates to alkyl 2-thiosubstituted-3-substituted-2-butenoates and to a method for their synthesis.

Alkyl 2-thiosubstituted-3-substituted-2-butenoates are useful intermediate products for the production of antibiotics and other compounds.

General background of synthesis routes to related compounds is provided by Durman, et al, *Alkylation of Extended Enolates from α-Phenylthio Crotonate Esters*, Tetrahedron Letters, Vol. 24, No. 20, p. 2113–2116 (1983); Takaki, et al, *Synthesis and Chemical Properties of α-Alkyl(aryl)thiovinyl Isocyanates*, J. Org. Chem., Vol. 43, No. 3, p. 402–405 (1978); and Rosnati, et al, *The $Ad_NS_NE$ Mechanism in the Reaction of Phenol and Benzenethiol with α-Bromo Michael Acceptors in the $K_2CO_3$-Acetone System*, Gazzetta Chemica Italiana, Vol. 111, p. 249–256 (1981).

SUMMARY OF THE INVENTION

Briefly, in one aspect the invention is a method of preparing an alkyl 2-thiosubstituted-3-substituted-2-butenoate comprising reacting an alkyl 2-chloro-3-substituted-3-butenoate with a thio compound under phase transfer conditions.

In another respect, the invention is the compound produced by the above method.

DETAILED DESCRIPTION OF THE INVENTION

In this specification and claims, numerical values are not critical unless otherwise stated. That is, the numerical values may be read as if they were prefaced with the word "about" or "substantially".

The invention is concerned with the synthesis of alkyl 2-thiosubstituted-3-substituted-2-butenoates. Such compounds have the general formula:

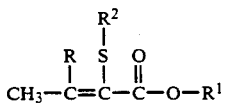

wherein R is a $C_1$ to $C_{12}$ organic moiety, preferably hydrocarbon moiety, more preferably a $C_1$ to $C_6$ hydrocarbon moiety; $R^1$ is a $C_1$ to $C_{12}$, desirably $C_2$ to $C_8$, preferably $C_2$ to $C_4$, and most preferably $C_2$ alkyl moiety; and $R^2$ is a $C_6$ to $C_{18}$ organic moiety, and preferably is a phenyl or thiazin moiety.

According to the invention, alkyl 2-thiosubstituted-3-substituted-2-butenoates are made from alkyl 2-chloro-3-substituted-3-butenoates. Such compounds have the general formula:

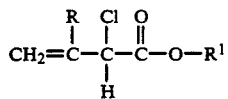

wherein R and $R^1$ are as defined above.

The alkyl 2-chloro-3-substituted-3-butenoate is reacted with a thio compound, H—S—$R^2$ or S=$R^2$, wherein $R^2$ is as defined above, under phase transfer alkylation conditions. Such conditions desirably include a solvent such as tetrahydrofuran, a phase transfer catalyst such as quaternary ammonium salts, for instance, tetrabutyl ammonium bromide, and a base such as an alkali metal hydroxide (preferably NaOH). The reaction can take place at room temperature within two hours. The reaction product mixture can be purified by extraction with ether and subsequent evaporation of the ether. If R is not —$CH_3$, then the reaction product will be a mixture of Z and E geometric isomers.

The invention will be further explained in the following examples. In the examples, all parts and percentages are by weight unless otherwise specified.

EXAMPLE 1

A mixture of thiophenol (0.7 g, 6.36 millimole), ethyl 2-chloro-3-methyl-3-butenoate (1.05 g, 6.5 millimole), tetrahydrofuran (2 ml), and tetrabutyl ammonium bromide (50 mg) was stirred at room temperature while one equivalent (1.5 ml) of 4N NaOH was added rapidly. Stirring of the resulting two-phase system was continued for two hours (at room temperature). The reaction mixture was diluted with 50 ml of water and extracted twice with 20 ml proportions of ether. Evaporation of the ether left 1.4 g of a crude yellow oil. Flash column chromatography on silica gel gave the desired product, ethyl 2-thiophenyl-3-methyl-2-butenoate in 66% overall yield. The identity of the product was confirmed by proton NMR, carbon 13 NMR, and mass spectrum analysis.

EXAMPLE 2

4-thiono-1,2,5-6,7,8-pentahydro,3,1,2-benzothiazine-2-spirocyclohexane, having the structure:

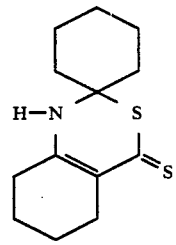

(0.7 g, 2.76 millimole), ethyl 2-chloro-3-methyl-3-butenoate (0.46 g, 1.1 equivalent), tetrabutyl ammonium bromide (50 mg), and tetrahydrofuran (2 ml) were stirred at room temperature while 4N NaOH (0.8 ml, 1 equivalent) was rapidly added. Stirring continued for 30 minutes until the red suspension had turned to a clear yellow. The reaction mixture was diluted with ether and water (20 ml of each) and the organic layer washed with water (10 ml) and dried over magnesium sulfate. Evaporation of the solvent gave 0.9 g of a brown oil. Flash column chromatography isolated the desired ethyl 2-thiazinethione-3-methyl-2-butenoate as a pale orange oil (0.6 g, 62% overall yield). The structure was confirmed as in Example 1.

EXAMPLE 3

Generally following the procedure of Example 1, ethyl 2-chloro-3-phenyl-3-butenoate was used to prepare ethyl 2-phenylthio-3-phenyl-2-butenoate to produce a mixture of isomers which could not be separated by flash column chromatography.

What is claimed is:

1. A method of preparing an alkyl 2-thiosubstituted-3-substituted-2-butenoate comprising reacting a. an alkyl 2-chloro-3-substituted-3-butenoate of the formula $$CH_2=\overset{R}{\underset{H}{C}}-\overset{Cl}{\underset{|}{C}}-\overset{O}{\overset{\|}{C}}-O-R^1$$

wherein R is a $C_1$ to $C_{12}$ hydrocarbon moiety and $R^1$ is a $C_1$ to $C_{12}$ alkyl moiety; and b. a thio compound of the formula:

$$H-S-R^2 \text{ or } S=R^2$$

wherein $R^2$ is a phenyl or a thiazine moiety; under phase transfer alkylation conditions.

2. The method of claim 1 wherein R is a $C_1$ to $C_6$ hydrocarbon moiety.

3. The method of claim 1 wherein $R^1$ has 2 to 8 carbon atoms.

4. The method of claim 3 wherein $R^1$ has 2 to 4 carbon atoms.

5. The method of claim 1 wherein phase transfer alkylation conditions include the use of the phase transfer alkylation catalyst which is a quaternary ammonium salt and an alkali metal hydroxide.

6. An alkyl 2-thiosubstituted-3-substituted-2-butenoate compound of the formula:

$$CH_3-\overset{R}{\underset{|}{C}}=\overset{\overset{R^2}{|}}{\underset{|}{\overset{S}{C}}}-\overset{O}{\overset{\|}{C}}-O-R^1$$

wherein R is a $C_1$ to $C_{12}$ hydrocarbon moiety, $R^1$ is a $C_1$ to $C_{12}$ alkyl moiety, and $R^2$ is a phenyl or a thiazine moiety.

7. The compound of claim 6 wherein R is a $C_1$ to $C_6$ hydrocarbon moiety.

8. The compound of claim 6 wherein $R^1$ has 2 to 8 carbon atoms.

9. The compound of claim 8 wherein $R^1$ has 2 to 4 carbon atoms.

* * * * *